Figure 1:
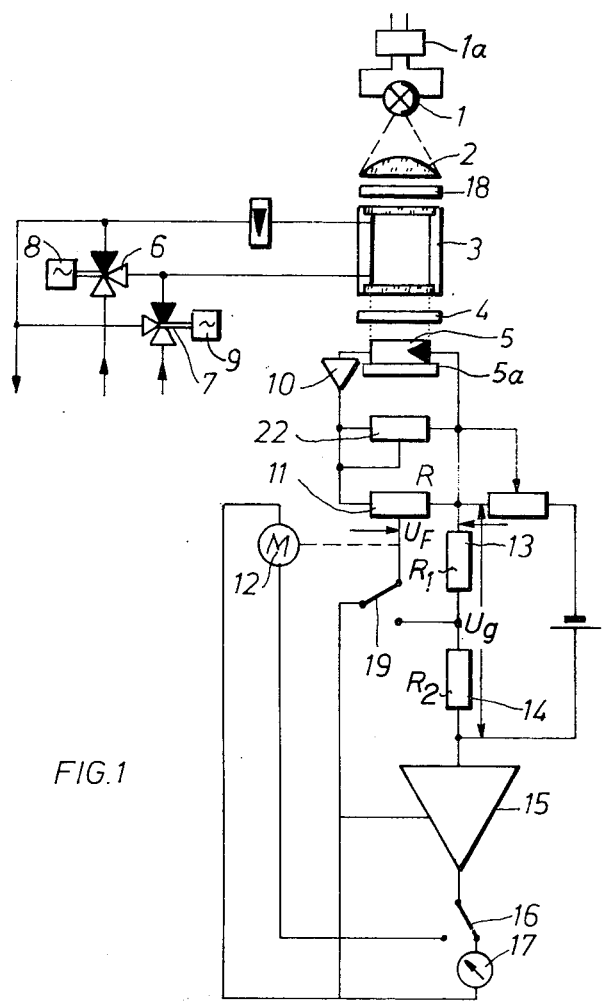

United States Patent [19]
Warncke

[11] 3,932,040
[45] Jan. 13, 1976

[54] SELF-EQUALIZING INDUSTRIAL PHOTOMETER

[75] Inventor: Heinz Warncke, Cologne, Germany

[73] Assignee: Bayer Aktiengesellschaft, Leverkusen, Germany

[22] Filed: June 20, 1973

[21] Appl. No.: 371,903

[30] Foreign Application Priority Data
June 23, 1972 Germany............................ 2230731

[52] U.S. Cl. ................ 356/201; 250/264; 250/573; 356/218
[51] Int. Cl.² ........................................ G01N 21/26
[58] Field of Search ........................... 250/573–576, 250/564, 565; 356/181, 201, 188, 204–208, 218

[56] References Cited
UNITED STATES PATENTS
3,622,795  11/1971  Dorman et al...................... 250/576

Primary Examiner—Vincent P. McGraw
Assistant Examiner—F. L. Evans
Attorney, Agent, or Firm—Burgess, Dinklage & Sprung

[57] ABSTRACT

The industrial photometer consists in principle of an optical single-beam measuring arrangement with the gas (or liquid) to be investigated flowing through the measuring cell. The detector behind the measuring cell consists of a photoelectric receiver which is connected to a working resistor with a remote-controlled voltage tap. A highly constant counter voltage is connected in series with the photovoltage. The measuring cell is filled at preselected time intervals with an absorption-free zero substance (standard substance), and the difference between the photovoltage and the constant voltage is automatically equalised to zero. After equalisation, the zero substance is again replaced by the measuring gas or liquid. The voltage difference then measured is a measure of the concentration to be determined.

11 Claims, 2 Drawing Figures

SELF-EQUALIZING INDUSTRIAL PHOTOMETER

This invention relates to an industrial photometer for the continuous automatic analysis of gaseous or liquid process streams.

Continuous, automatic analysers are used to a steadily increasing extent for process control, for safety purposes or for protection of the environment. These automatic apparatus require regular checking and maintenance which, in the past, has mainly been carried out by hand. In order to further rationalise process analysis, therefore, the checking routine should be automated as far as possible.

This applies in particular to industrial photometers which are used for measuring corrosive gases or which function in the UV-range because they require particularly frequent zero-point and sensitivity checks. Despite effective filtering and preparation of the measured substance, it is not possible to avoid corrosion-induced changes in the measuring zone and window deposits through photochemical reactions in the short-wave measuring light. The daily or even more frequent checks and adjustments necessitated involve considerable maintenance work. In addition, the change in the measuring zone is frequently so rapid that the required accuracy of measurement can only be maintained for a relatively short period after calibration. In a conventional two-beam photometer, these changes naturally affect only the measuring branch and not the comparison branch, so that advantages of the two-beam process are lost.

Initially, attempts were made to find a solution to this problem by applying a bichromatic one-cell process. The measuring light and comparison light differing in wavelength pass through the same cell traversed by the measured substance, but it is only the measuring wavelength that is absorbed by the measured component. By measuring the ratio between the two light intensities, it is possible in this way to compensate for contaminations of the cell provided the contaminations absorb both wavelengths to the same extent. Unfortunately, the window and cell coatings generally do not have a grey effect, but instead show greater absorption of the shorter wavelengths (scattering, UV-absorption). Accordingly, the bichromatic process genrally cannot be used to compensate for cell coatings.

The only useful alternative is a genuine substitution method, in which the zero gas and standard gas are introduced into the measuring cell at relatively short time intervals and zero-point and sensitivity are automatically equalised. Apparatus for automatic zero and standard control in which the measured value is electronically stored during the equalising process, were developed for this purpose. However, they involve considerable additional outlay. Another disadvantage is that, in addition to a zero gas (absorptionfree), a deflection gas (with known absorption) has to be kept permanently ready. This is difficult or even totally impossible in the case of condensible, corrosive or toxic measured components.

Accordingly, the object of the invention is to provide an industrial photometer which
1. contains an automatic equalizing system,
2. effects this automatic equalisation without additional outlay, and
3. only requires the readily prepared zero substance.

According to the invention, there is therefore provided an industrial photometer for the continuous automatic analysis of gaseous or liquid process streams, consisting of an optical single-beam measuring arrangement incorporating a light source, a measuring cell through which the process stream flows, a spectral filtering means and a photoelectric receiver whose electrical signal, in the absence of luminous flux, is also zero and which shows adequate linearity between luminous flux and photocurrent for the measuring wavelength and measuring light intensity selected, comprising a photoelectric receiver connected to a working resistor having a remote-controlled voltage tap, the tapped voltage being proportional to the luminous flux, means for producing a highly constant counter voltage connected in series with the tapped voltage whereby difference between the tapped voltage and the counter voltage is formed in a differential circuit, a measuring cell which may be connected at preselected time intervals to a zero substance source so that the process stream in the measuring cell is automatically replaced for a fixed time interval by a zero substance which does not have any absorption at the measuring wavelength, a regulating device for automatically equalising the tapped voltage and the counter voltage at the end of this time interval by varying the tapped voltage, and valves provided in the pipes through which the zero substance and the process stream flow to the measuring cell, which are actuated by control circuits in such a way that, on completion of the zero adjustment, the zero substance in the measuring cell is automatically replaced by the process stream.

The constant voltage $U_g$ selected is with advantage in a fixed ratio to the voltage measuring range of the visual indicators which are acted on by the voltage difference $U_f - U_g$, this voltage ratio determining the optical measuring range of the arrangement. In this way, both the zero-point and also the sensitivity of the measuring arrangement are determined solely by the zero adjustment with the zero substance.

One preferred embodiment includes a d.c. voltage amplifier for amplifying the voltage difference $U_f - U_g$. The output of this amplifier is switched to the visual indicators during the measuring period and, at the end of the zero period, is switched for automatic equalisation to a servo motor which drives the voltage tap on the working resistor. Accordingly, the d.c. voltage amplifier acts as a measuring amplifier during the measuring period and, during the zero period, as a power amplifier for driving the voltage tap on the working resistor.

A feedback preamplifier is with advantage connected between the photoelectric receiver and the working resistor. In this way, the working impedance of the photoelectric receiver determining linearity between luminous flux and photocurrent is reduced.

In many cases, it is best to work with a suppressed zero-point. If, for example, the concentration to be measured is in the range from 80 to 100 %, the full measuring range should correspond to a change in concentration of 20 %. According to another aspect of the invention, therefore, the zero-substance is temporarily replaced by a standard substance which contains the measured component, the concentration of the measured component in the standard substance being equal to the initial value or end value of the required concentration range.

If the required measuring range does not include the end value of 100 % it is nevertheless still possible to effect an equalisation with a suppressed zero-point, providing the measuring cell is preceded by an auxiliary cell which is filled during the measuring period with a non-absorbing medium and during the zero period with the measuring component in pure form (100 % concentration), whilst the measuring cell contains the non-absorbing medium. The layer thickness of the auxiliary cell in relation to the layer thickness of the measuring cell is such that the absorption of the pure measuring component in the auxiliary cell is equal to the absorption in the measuring cell at the beginning or end point of the measuring range.

In one improved embodiment of the invention, the supply voltage for the light source is stabilised and the photoelectric receiver thermostatically controlled.

According to one particularly advantageous embodiment of the invention, the optical measuring zone is in the form of a remote measuring head and is separated in space from the electronic evaluating and equalising unit.

The advantages afforded by the invention are essentially embodied in the fact that zero control can be carried out during operation. In the most simple case, the zero substance is air which is available practically everywhere. Another particular advantage is embodied in the ready adaptability of the measuring range. By suitably selecting the counter voltage $U_g$, it is possible to adjust the sensitivity of the apparatus within wide limits. Zero-point suppression is also readily possible.

Another advantage of the invention is embodied in the relatively simple electronics used. The apparatus functions in the direct-current range and, for this reason, does not require any interrupters in the beam path. Finally, it is pointed out that the single-beam measuring arrangement allows the construction of a compact remote measuring head which can be separated from the electronics.

Embodiments of the invention are described by way of example in the following with reference to the accompanying drawings, wherein:

FIG. 1 diagrammatically illustrates the structure of an industrial photometer according to the present invention with a measuring and equalising circuit.

Figure 2:
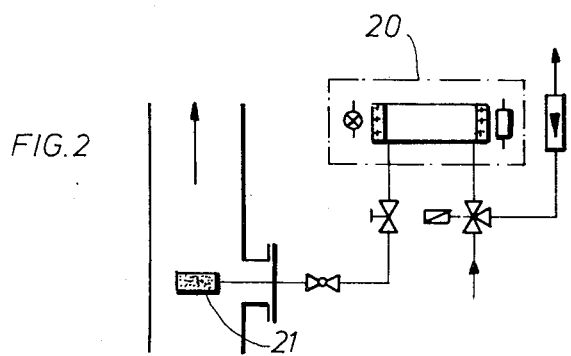

FIG. 2 illustrates the structure of the remote measuring head.

According to FIG. 1, the optical part of the industrial photometer consists of the light source 1, the condenser 2, the measuring cell 3, the interference filter 4 and the photoelement 5. The measuring cell 3 is connected through threeway magnetic valves with the process stream, the zero substance and an exhaust-gas pipe. The threeway magnetic valves 6, 7 are actuated by electrical programme controls 8, 9. For reasons of stability, the light source 1 is powered by a stabilised power supply unit 1a. For the same reasons, the temperature-sensitive photoelement 5 is mounted on a thermostatically controlled metal plate 5a.

The output current of the photoelement 5 is amplified by a feedback amplifier 10 and delivered to the working resistor R in the form of a motor potentiometer 11. The voltage tap of the motor potentiometer 11 can be adjusted by the motor 12. A hand potentiometer 22 is connected in parallel with the working resistor 11, being used for rough zero-point adjustment. The signal coming from the preamplifier can hence be adjusted so that the motor potentiometer 11 always works around the middle of its adjusting range. The voltage drop $U_f$ produced in the motor potentiometer 11 is compared with a highly constant counter voltage $U_g$ in a differential circuit. The differential circuit consists essentially of the working resistor 11, the voltage-dividing resistors 13, 14 ($R_1$ and $R_2$) and of the operating amplifier 15. The voltage difference $U_f - U_g$ is amplified by the operating amplifier 15 to the unit range 0 – 20 mA and is switched through a reversing switch 16 either to the measuring instrument 17 or to the servomotor 12. The measuring arrangement is safeguarded against temporary fluctuations by the already mentioned stabilisation of the feed voltage and temperature regulation of the photoelement (and optionally even of the entire measuring zone).

Residual long-duration disturbance variables are then the coating of the cell window and ageing phenomena of the light source, of the interference filter and of the photoelement. An automatic equalising operation is carried out to compensate for the disturbance variables. To this end, the zero substance (air) flows through the measuring cell 3 by way of the two three-way magnetic valves 6 and 7 at preselected time intervals (for example every 30 minutes) for a period of 1 to 2 minutes (depending upon the cell volume) [zero period]. The pneumatic circuit of the two threeway valves is selected in such a way that, even in the event of slight leaks in the valves in the blocking direction, there can never be any false measurements either in the measuring position or in the equalising position.

At the end of the zero period, the output of the operating amplifier 15 is switched for a few seconds to the servomotor 12 by means of the switch 16 and the differential between the photovoltage $U_f$ and the counter voltage $U_g$ is reduced to zero. The counter voltage $U_g$ remains switched off even during the following measuring period, so that the output signal zero is also obtained for the zero concentration of the measuring component. The photovoltage becomes lower as the concentration of the measuring component increases, so that its difference in relation to the counter voltage is measured of the concentration of the component being measured.

The optical measuring range of the arrangement is determined solely by the ratio of the counter voltage to the measuring range of the indicating instrument 17, based on the amplifier input. If the measuring range and counter voltage are the same, the optical range of 0 to 100 % absorption is obtained. With partial absorption ranges, the counter voltage must be a corresponding multiple of the measuring range (i.e., for example the factor 4 for 0 to 25 % light absorption). The relationship between concentration and light absorption is thus determined by the layer thickness of the measuring cell 3 and the molar extinction at the measuring wavelength. For these reasons, equalisation with the zero substance is in itself sufficient to establish the zero-point and sensitivity of the arrangement.

Measuring ranges with a suppressed zero-point are also possible in cases where a standard substance corresponding to the beginning or end point of the measurement range is available. Thus, equalisation to the end point 100 % by volume is carried out for example for the measuring range 80 to 100 % by volume with the pure measuring component. In this case, the measuring effect is not an absorption of light, but a brightening effect, in comparison with the equalising point. The ratio of luminous flow with 80 % by volume of measuring component to luminous flow with 100 % of measuring substance is again determined solely by layer thickness and molar extinction. The measuring and equalising operations take place as before, except that the sign of the difference between photovoltage and counter voltage is reversed. The measuring substance is, for example, the concentration to be determined of a foreign substance in the process stream.

If the required measuring range does not include the 100 % point, it is possible inspite of this to find a simple method of carrying out the automatic equalisation with the pure measuring component (100 %). For this purpose, the measuring cell 3 is preceded by an auxiliary cell 18 whose layer thickness in relation to the layer thickness of the measuring cell is such that the absorption of the pure measuring component in the auxiliary cell 18 is equal to the absorption in the measuring cell 3 at the beginning or end of the measuring range.

The motor potentiometer 11 is equipped with a second coupled potentiometer (not shown in FIG. 1) which is used to convert the position of the motor potentiometer into an electrical indication. Regular checking of the apparatus is initially confined to checking the position of the automatic equalising system. When it approaches one end of its adjusting range, it is brought back into the middle of its adjusting range by resetting the hand potentiometer to "rough zero-point." It is only after this manual equalisation has reached the end of its adjusting range that the optical measuring zone has to be serviced (cleaning the cell, changing the light source or detector). The automatic equalisation system is designed in such a way that zero-substance rinsing and equalisation can be initiated not only by the programmer installed but also by hand or by remote-control (computer).

In order to adjust the counter voltage, the switch 19 is brought into the testing position and a component of the counter voltage $U_g$ measurably reduced by the resistance ration $R_1:R_2$ is measured: This is necessary to bring the occasionally very much higher counter voltage into the measuring range of the operating amplifier 15. In this way, the accuracy of the counter voltage is determined solely by the ratio $R_1:R_2$ and not by the amplification of the operating amplifier. The long-term stability of the counter voltage source has to meet stringent requirements, although this does not involve any problems.

Self-equalising photometer with a remote measuring head

Conventional industrial photometers are generally very susceptible to harsh environmental conditions and, for this reason, are usually installed in protective atmospheres. Relatively long cables or relatively long dead times often have to be accepted. In the past, however, this was the only possibility of guaranteeing satisfactory service life and substantially interference-free operation. Now that maintenance of the optical section has been reduced to a minimum in the self-equalising photometer of the present invention and the optics confined to a very simple single-beam arrangement, it is possible to design the optical measuring zone in the form of a remote measuring head 20 for direct use at the measuring site. The need for optical image-forming elements is also eliminated in the case of relatively small layer thicknesses. Minimum maintenance of the measuring head and automatic equalisation are requirements that have to be satisfied for this purpose. FIG. 2 shows such an arrangement for measuring substances at excess pressures of up to about 1 bar. In this case, rinsing of the cell with the zero substance is also used for backwashing the internal filter 21 at the orifice of the sampling probe in the process stream. The relatively simple optical remote measuring head 20 with its relatively low dissipation factor is also easier to protect against explosion than a complete industrial photometer.

What we claim is:

1. A photometer for the continuous automatic analysis of gaseous or liquid process streams, comprising an optical single-beam measuring arrangement incorporating a light source, a measuring cell through which the process stream flows, a spectral filtering means and a photoelectric receiver whose electrical signal, in the absence of luminous flux, is zero and which shows adequate linearity between luminous flux and photocurrent for the measuring wavelength and measuring light intensity selected, and further comprising
    a. a working resistor having a remote-controlled voltage tap, the tapped voltage being proportional to the luminous flux, connected to said photoelectric receiver,
    b. means for producing a highly constant counter voltage connected in series with the tapped voltage and a differential circuit for forming the difference between the tapped voltage and the counter voltage,
    c. said measuring cell being adapted to be connected at preselected time intervals to a zero substance source so that the process stream in the measuring cell is automatically replaced for a fixed time interval by a zero substance which does not have any absorption at the measuring wavelength, and
    d. a regulating device for automatically equalizing the tapped voltage and the counter voltage at the end of this time interval by varying the tapped voltage.

2. A photometer as claimed in claim 1, and a visual indicator which is acted upon by the voltage difference between the tapped voltage and the counter voltage, the counter voltage being a fixed ratio to the voltage measuring range of the visual indicator, this ratio determining the optical measuring range of the arrangement so that both the zero-point and also the sensitivity of the measuring arrangement are determined solely by the zero adjustment with the zero substance.

3. A photometer as claimed in claim 2, further comprising a d.c. voltage amplifier for amplifying the voltage difference and a servomotor which drives the voltage tap on the working resistor, and means for switching the output of the voltage amplifier to the visual indicator during the measuring period, and, at the end of the zero period, to the servomotor for automatic equalization.

4. A photometer as claimed in claim 1, wherein a feedback preamplifier is connected between the photoelectric receiver and the working resistor so that the working impedance of the photoelectric receiver determining linearity between luminous flux and photocurrent is sufficiently low.

5. A photometer as claimed in claim 1 and means permitting the measurements to be carried out with a suppressed zero point, whereby the zero substance may be temporarily replaced by a standard substance containing the measured component in a concentration equal to the initial value or end value of the required concentration range.

6. A photometer as claimed in claim 1, comprising a condenser for collimating the light from the light source, and an auxiliary cell arranged between the measuring cell and the condenser, which auxiliary cell may be filled during the measuring period with a non-absorbing medium and, during the zero period, with the measuring component in pure form, whilst the measuring cell contains a non-absorbing medium.

7. A photometer as claimed in claim 1, and means for stabilizing supply voltage for the light source and means for thermostatically controlling the photoelectric receiver.

8. A photometer as claimed in claim 1, wherein the optical measuring zone is in the form of a remote measuring head and is separated in space from the electronic evaluating and comparison unit.

9. A photometer as claimed in claim 1, and a conduit system including valves, for flow of the zero substance and the process stream to the measuring cell, and control means for actuating the conduit system so that, on completion of zero adjustment, the zero substance in the measuring cell is automatically replaced by the process stream.

10. A photometer as claimed in claim 1, and means for temporarily replacing the zero substance by a standard substance containing the measured component in a concentration equal to the initial value or end value of the required concentration range for operating the device with suppressed zero point.

11. A photometer as claimed in claim 1, comprising an auxiliary cell arranged between the measuring cell and the light source, which auxiliary cell may be filled during the measuring period with a non-absorbing medium and, during the zero period, with the measuring component in pure form, whilst the measuring cell contains a non-absorbing medium.

* * * * *